United States Patent [19]

Muroi et al.

[11] 4,421,688
[45] Dec. 20, 1983

[54] MACBECIN DERIVATIVES

[75] Inventors: Masayuki Muroi, Suita; Makoto Kida, Kawanishi, both of Japan

[73] Assignee: Takeda Chemical Industries, Ltd., Osaka, Japan

[21] Appl. No.: 414,032

[22] Filed: Sep. 2, 1982

[30] Foreign Application Priority Data

Sep. 17, 1981 [JP] Japan ................................ 56-147175

[51] Int. Cl.$^3$ ........................................... C07D 225/06
[52] U.S. Cl. .............................. 260/239.3 B; 435/128; 435/872; 424/244
[58] Field of Search ................................. 260/239.3 B

[56] References Cited

U.S. PATENT DOCUMENTS 4,187,292  2/1980  Higashide et al. .

OTHER PUBLICATIONS

*Journal of Antibiotics*–vol. XXXIII, 1980, Japan Antibiotics Res. Association, Tokyo, pp. 1114–1119.
*Tetrahedron Letters*–Oct. 1979, No. 41, Pergamon Press Int. Journal for Rapid Publication . . . Organic Chemistry, pp. 4323–4326.
*Tetrahedron Letters*, vol. 21, No. 1, Pergamon Press, 1980, Int. Journal for Rapid Publication . . . Organic Chemistry, pp. 309–312.
*Tetrahedron Letters*, vol. 37, No. 6, 1981, Pergamon Press Int. Journal for Rapid Publication . . . Organic Chemistry, pp. 1123–1130.
*Journal of American Chemical Society*, vol. 92, 1970, pp. 7591–7593.
*Journal of the American Chemical Society*, vol. 96, 1974, pp. 3316–3317.

*Primary Examiner*—Robert T. Bond
*Attorney, Agent, or Firm*—Wenderoth, Lind & Ponack

[57] ABSTRACT

Macbecin derivatives are produced by bringing Macbecins into contact with a microorganism, or its processed matter, of the genus Streptomyces or Nocardia. The Macbecin derivatives are useful as antibacterial, antifungal or antiprotozoal agent.

7 Claims, No Drawings

MACBECIN DERIVATIVES

The present invention relates to novel Macbecin derivatives having antibacterial and other activities and methods of producing the same.

Antibiotics c-14919E-1 and E-2 were isolated as novel antibiotics (Japanese Patent Application Laid-open (unexamined) No. 121704/1978 and 121705/1978). Later, their structures were determined and they were named Macbecin I and II, respectively [e.g. Tetrahedron Letters, vol. 21, No. 3, p. 309 (1980)].

The inventors, i.e. Masayuki Muroi and Makoto Kida, searched for a method of converting Macbecin I and II into other compounds by the aid of a microorganism and found that treatment of Macbecin I or II with the culture broth of a certain microorganism or a processed matter derived therefrom converts it into a compound having a hydroxy group instead of the methoxy group at a certain position. Further research by the inventors based on this finding has led to the present invention.

In search of novel antibiotics, the inventors, i.e. Toru Hasegawa, Masayuki Muroi and Seiichi Tanida, isolated a great number of microorganisms from soil and other sources, searched for antibiotics produced by the microorganisms and found that some are antibiotic-producing microorganisms, that said microorganisms belong to the genus Actinosynnema, and that antibiotics exhibiting activity against gram-positive bacteria, fungi and protozoa can be accumulated in appropriate media by cultivating said microorganisms in the media. They isolated and purified the antibiotics and, based on their characteristic properties, recognized them as novel macbecin-related compounds, and named as Antibiotics c-33196 E-3, E-3-R, E-4, E-4-R, E-5, E-5-R, E-6, E-6-R, E-7 and E-7-R. As a result of further research based on the above findings, the inventors have completed the present invention.

Thus, the present invention relates to (1) Macbecin derivatives of the formula:

(I)

wherein one of $R_1$, $R_2$ and $R_3$ is hydrogen and each of the remaining two is methyl and X is or

, (2) a method of producing Macbecin derivatives of the formula:

(I)

wherein one of $R_1$, $R_2$ and $R_3$ is hydrogen and each of the remaining two is methyl and X is or

, which comprises bringing a compound of the formula:

(II)

wherein X is as defined above, into contact with the culture broth obtained by cultivating a microorganism belonging to the genus Streptomyces or Nocardia and capable of converting the methoxy group at position 17, 18 or 21 of said compound (II) into a hydroxy group or a processed matter derived from said culture broth, (3) Antibiotic C-33196 E-4 or C-33196 E-4-R, which has the following properties:

(a) Antibiotic C-33196E-4:

(I) Melting point: 209°–210° C.

(II) Appearance: Yellow crystals (III) Specific rotation: $[\alpha]_D^{25} + 53° \pm 5°$ (c=0.5, CHCl$_3$)

(IV) Elemental analysis (%): C 63.14±0.5; H 7.57±0.5; N 5.25±0.5

(V) Mass spectrum (M+): m/z 532

(VI) Ultraviolet absorption spectrum: $\lambda_{max}^{MeOH}$ 276 nm±2 ($E_{1cm}^{1\%}$ 272±20); 390 nm±2 ($E_{1cm}^{1\%}$ 33.5±5)

(VII) Infrared absorption spectrum, principal peaks (cm$^{-1}$): 1735, 1700, 1670, 1650, 1625, 1605, 1500, 1380, 1305, 1290, 1210, 1050

(VIII) Solubility: Sparingly soluble in petroleum ether, hexane, water; Soluble in chloroform, methylene chloride, toluene, diethyl ether; Readily soluble in acetone, ethyl acetate, methanol, dimethyl sulfoxide (IX) Color reactions: Positive potassium permanganate test (decoloration); Negative ninhydrin, Ehrlich and Barton reactions (X) Acidity, neutrality or basicity: Neutral (b) Antibiotic C-33196E-4-R (properties of the crystals containing one molecule of ethyl acetate as the solvent of crystallization):

(I) Melting point: 224°–225° C.

(II) Appearance: Colorless crystals (III) Specific rotation: $[\alpha]_D^{25} +32°\pm5°$ (c=0.5, MeOH)

(IV) Elemental analysis (%): C 60.96±0.5; H 8.25±0.5; N 4.59±0.5

(V) Mass spectrum (M+): m/z 534

(VI) Ultraviolet absorption spectrum: $\lambda_{max}^{MeOH}$ 307 nm+2 nm ($E_{1cm}^{1\%}$ 75±8)

(VII) Infrared absorption spectrum, principal peaks (cm$^{-1}$): 1720, 1670, 1630, 1600, 1535, 1465, 1380, 1325, 1045

(VIII) Solubility: Sparingly soluble in petroleum ether, hexane, diethyl ether, chloroform and ethyl acetate; Soluble in methanol; Readily soluble in dimethyl sulfoxide (IX) Color reactions: Positive Barton reaction; Negative ninhydrin and Ehrlich reactions (X) Acidity, neutrality or basicity: Neutral, (4) Antibiotic C-33965 E-6, C-33196 E-6-R, C-33196 E-7 or C-33196 E-7-R, which has the chemical structure:

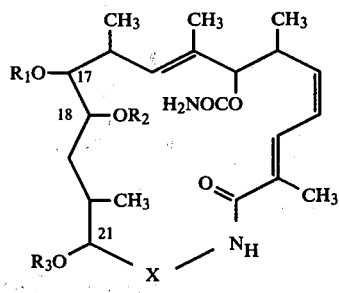

wherein one of the groups of $R_1$, $R_2$ and $R_3$ is methyl and the remaining ones are hydrogen, and X is a group of

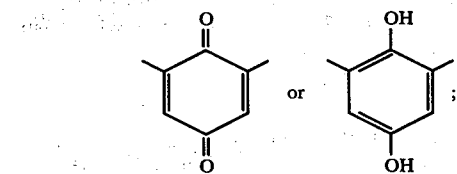

and has the following properties:

(a) Antibiotic C-33196 E-6:

(I) Specific rotation: $[\alpha]_D^{24} +258.8°\pm20°$ (c=0.5, CHCl$_3$)

(II) Ultraviolet absorption spectrum: $\lambda_{max}^{MeOH}$ 273 nm±2 nm ($E_{1cm}^{1\%}$ 454±45); $\lambda_{max}^{MeOH}$ 397 nm±2 nm ($E_{1cm}^{1\%}$ 50.3±5)

(III) Infrared absorption spectrum, principal peaks (cm$^{-1}$): 1720, 1705, 1670, 1650, 1610, 1505, 1380, 1325, 1265, 1210, 1090, 1040.

(b) Antibiotic C-33196 E-6-R:

(I) Specific Rotation: $[\alpha]_D^{24} +37.8°\pm4°$ (c=0.5, MeOH)

(II) Ultraviolet absorption spectrum: $\lambda_{max}^{MeOH}$ 255 nm±2 nm ($E_{1cm}^{1\%}$ 337±30); $\lambda_{max}^{MeOH}$ 307 nm±2 nm ($E_{1cm}^{1\%}$ 91±9)

(III) Infrared absorption spectrum, principal peaks (cm$^{-1}$): 1720, 1650, 1600, 1535, 1460, 1380, 1320, 1090, 1040, 1010

(c) Antibiotic C-33196 E-7:

(I) Specific rotation: $[\alpha]_D^{24} +37.4°\pm4°$ (c=0.5, CHCl$_3$)

(II) Ultraviolet absorption spectrum: $\lambda_{max}^{MeOH}$ 274 nm±2 nm ($E_{1cm}^{1\%}$ 502±50); $\lambda_{max}^{MeOH}$ 396 nm±2 nm ($E_{1cm}^{1\%}$ 59.8±6)

(III) Infrared absorption spectrum, principal peaks (cm$^{-1}$): 1725, 1670, 1650, 1605, 1500, 1380, 1325, 1260, 1205, 1150, 1095, 1035

(d) Antibiotic C-33196 E-7-R:

(I) Specific rotation: $[\alpha]_D^{24} +18.6°\pm2°$ (c=0.5, MeOH)

(II) Ultraviolet absorption spectrum: $\lambda_{max}^{MeOH}$ 250 nm±2 nm ($E_{1cm}^{1\%}$ 305±30); $\lambda_{max}^{MeOH}$ 315 nm±2 nm ($E_{1cm}^{1\%}$ 68±7)

(III) Infrared absorption spectrum, principal peaks (cm$^{-1}$): 1710, 1640, 1600, 1485, 1455, 1380, 1310, 1250, 1090, 1040, and (5) a method of producing Antibiotic C-33196 E-3, C-33196 E-3-R, C-33196 E-4, C-33196 E-4-R, C-33196 E-5, C-33196 E-5-R, C-33196 E-6, C-33196 E-6-R, C-33196 E-7 or C-33196 E-7-R, which comprises cultivating a microorganism belonging to the genus Actinosynnema which is able to produce Antibiotic C-33196 E-3, C-33196 E-3-R, C-33196 E-4, C-33196 E-4-R, C-33196 E-5, C-33196 E-5-R, C-33196 E-6, C-33196 E-6-R, C-33196 E-7 or C-33196 E-7-R in a culture medium to cause said microorganism to elaborate and accumulate said compound in the culture broth and harvesting said compound from the culture broth.

The compound of the formula (I) in which $R_1$, $R_2$ and $R_3$ each is methyl and X is

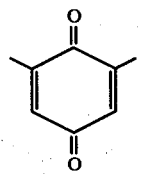

is called "Macbecin I", and the compound of the above structural formula (I) in which $R_1$, $R_2$ and $R_3$ each is methyl and X is

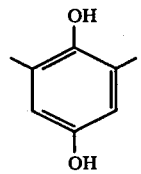

is called "Macbecin II" [cf. Japanese Patent Application Laid-open (unexamined) 121,704/1978, Japanese Patent Application Laid-open (unexamined) 121,705/1978, U.S. Pat. No. 4,187,292, Tetrahedron Letters, 21, 309 (1980), Tetrahedron, 37 (6), 1123 (1981)].

The compund of the formula (I), in which $R_1$ is hydrogen, $R_2$ and $R_3$ are methyl and X is

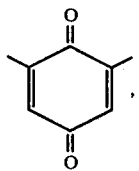

is named "Antibiotic C-33196 E-3", the compound of the formula (I), in which $R_1$ is hydrogen, $R_2$ and $R_3$ are methyl and X is

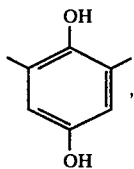

is named "Antibiotic C-33196 E-3-R", the compound of the formula (I), in which $R_1$ and $R_3$ are methyl, $R_2$ is hydrogen and X is

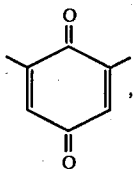

is named "Antibiotic C-33196 E-5", the compound of the formula (I), in which $R_1$ and $R_3$ are methyl, $R_2$ is hydrogen and X is

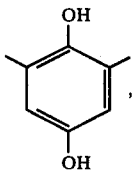

is named "Antibiotic C-33196 E-5-R", the compound of the formula (I), in which $R_1$ and $R_2$ are methyl, $R_3$ is hydrogen and X is

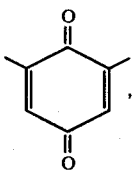

is named "21-O-demethylmacbecin I", and the compound of the formula (I), in which $R_1$ and $R_2$ are methyl, $R_3$ is hydrogen and X is

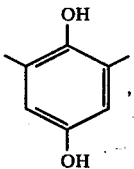

is named "21-O-demethylmacbecin II".

In this specification, Antibiotic C-33196 E-3 is sometimes referred to as "C-33196 E-3" or simply as "E-3", Antibiotic C-33196 E-3-R as "C-33196 E-3-R" or simply as "E-3-R", Antibiotic C-33196 E-4 as "C-33196 E-4" or simply as "E-4", Antibiotic C-33196 E-4-R as "C-33196 E-4-R" or simply as "E-4-R", Antibiotic C-33196 E-5 as "C-33196 E-5" or simply as "E-5", Antibiotic C-33196 E-5-R as "C-33196 E-5-R" or simply as "E-5-R", Antibiotic C-33196 E-6 as "C-33196 E-6" or simply as "E-6", Antibiotic C-33196 E-6-R as "C-33196 E-6-R" or simply as "E-6-R", Antibiotic C-33196 E-7 as "C-33196 E-7" or simply as "E-7" and Antibiotic C-33196 E-7-R as "C-33196 E-7-R" or simply as "E-7-R".

The microorganism to be used for the production of the compound (I) by converting the compound (II) may be any of microorganisms belonging to the genus Streptomyces or Nocardia and capable of converting the methoxy group at position 17, 18 or 21 of the compound (II) into a hydroxy group and mutants thereof. Examples of the microorganism which are usable according to the invention are *Streptomyces platensis* and *Nocardia mediterranei*, more specifically *Streptomyces platensis* IFO 12901 (ATCC 23948=13865) and *Nocardia mediterranei* ATCC 13685 (IFO 13415).

The above-mentioned IFO 12901 and IFO 13415 strains are listed in the Institute for Fermentation, Osaka, List of Cultures, 1978, Sixth Edition. The ATCC 23948 (=13865) and ATCC 13685 strains are listed in the American Type Culture Collection, Catalogue of Strains I, Fourteenth Edition, 1980 and Fifteenth Edition, 1982.

The morphological characteristics of *Streptomyces platensis* are described in International Journal of Systematic Bacteriology, vol. 18, No. 4, p. 360 (1968). The morphological characteristics of *Nocardia mediterranei* ATCC 13685 are described in Mycopathologia vol. 13, p. 321–330 (1960). The above ATCC 13685 strain was first classified under the genus Streptomyces but later reported as belonging to the genus Nocardia [see Archiv für Mikrobiologie, vol. 67, p. 147 (1969)].

The microorganisms of the genera Streptomcyes and Nocardia are, as a general trait, labile in their characteristic properties. Thus, mutants thereof can easily be obtained by artificial mutagenic treatments such as irradiaton with X-rays, ultraviolet ray or other rays or use of artificial mutagens (e.g. N-methyl-N'-nitro-N-nitrosoguanidine, ethyleneimine). Any of such mutants also can be used in practicing the method of the invention when it is capable of converting the methoxy group at position 17, 18 or 21 of compound (II) into a hydroxy group.

The medium for the cultivation of the above microorganism for use in the practice of the invention may be either a liquid or a solid medium as long as it contains nutrients which the strain can utilize, although a liquid medium is preferred for large scale treatment. The medium should adequately contain carbon and nitrogen sources assimilable or digestible by the above microorganism, inorganic substances, trace nutrients, and so forth. Examples of the carbon source are glucose, lactose, sucrose, maltose, dextrin, starch, glycerol, mannitol, sorbitol, fats and oils (e.g. soybean oil, lard oil, chicken oil) and the like. Examples of the nitrogen source are meat extract, yeast extract, dried yeast, soybean meal, corn steep liquor, peptone, cottonseed flour, spent molasses, urea, ammonium salts (e.g. ammonium sulfate, ammonium chloride, ammonium nitrate, ammonium acetate) and the like. The medium may further contain salts of sodium, potassium, calcium, magnesium, etc., salts of such metals as iron, manganese, zinc, cobalt and nickel, salts of phosphoric acid, boric acid, etc., and organic acid salts such as acetates and propionates. Furthermore, the medium may contain amino acids (e.g. glutamic acid, aspartic acid, alanine, glycine, lysine, methionine, proline), peptides (e.g. dipeptides, tripeptides), vitamins (e.g. $B_1$, $B_2$, nicotinic acid, $B_{12}$, C, E), nucleic acids (e.g. purines, pyrimidines, and derivatives thereof) and the like. For the purpose of adjusting the pH of the medium, there may be added an inorganic or organic acid, an alkali, a buffer, or the like. Suitable amounts of oils, fats, surfactants, etc. may also be added to the medium for the purpose of defoaming.

The cultivation may be conducted by any of the stationary, shake, submerged aerobic and other cultural method. For high production runs, submerged aerobic culture is of course preferred. While the cultivation conditions naturally vary depending on the state and composition of medium, the type of strain, cultural method and other factors, it is generally preferred to carry out incubation at about 20° C. to 45° C. with an initial pH of about neutral. Particularly desirable is a temperature of about 24° C. to 37° C. in the intermediate stage of cultivation, with an initial pH of about 6.5 to 8.5. The incubation time required normally ranges from about 6 to 100 hours, preferably from about 10 to 48 hours.

The "culture broth" to be used in accordance with the invention is the one obtained by the above cultivation.

The "processed matter" to be used according to the invention includes the microbial cells and demethylase-containing cell disintegration products which are obtained from the above culture broth by physical or chemical treatments such as filtration, centrifugation, ultrasonic treatment, French press treatment, grinding with alumina, treatment with lytic enzyme and treatment with a surfactant or organic solvent. It also includes the demethylase obtained by a conventional purification method and the cells or demethylase immobilized by a conventional method.

The method of the invention is practiced by bringing the starting compound (II) into contact with the culture broth of the above microorganism or a processed matter therefrom. The concentration of the starting compound (II) in the reaction mixture is preferably 10–1,000 μg/ml. The reaction temperature is preferably about 20°–50° C., more preferably about 24°–40° C., and the pH is preferably about 5–10, more preferably about 6–9. It is advisable to perform the reaction over a period of about 1–100 hours, preferably about 16–72 hours. The reaction may be carried out in the stationary, shaken, aerated or stirred condition although in the shaken, aerated or stirred condition is preferred.

If any one of compounds (I) alone is the reaction product, the desired compound (I) may be isolated in the crystalline form by merely extracting the culture broth with a water-immiscible organic solvent, for example ethyl acetate, followed by concentration of the extract. Generally, however, the reaction gives a mixture of compounds (I). Therefore, for the purpose of purification, it is preferable to convert compounds 21-O-demethylmacbecin II, E-5-R and E-3-R to the corresponding quinones using an oxidizing agent prior to the separation procedure. The oxidizing agent includes those oxidizing agents which are generally used for oxidation of hydroquinones to benzoquinones, such as ferric chloride, ferric sulfate and silver oxide.

In some cases, depending on the contents of compounds 21-O-demethylmacbecin I, E-5 and E-3 and impurities, it is preferable to treat the products in the form of hydroquinones. The compounds which are in the hydroquinone form, namely compounds 21-O-demethylmacbecin II, E-5-R and E-3-R are obtainable by reacting compounds 21-O-demethylmacbecin I, E-5 or E-3 with a reducing agent for use in the reduction of benzoquinones, such as sodium hydrosulfite.

The yield ratio among compounds 21-O-demethylmacbecin I, E-5 and E-3 varies depending on the kind of microorganism used and accordingly the method adequate for their purification may vary. Generally, however, those ordinary purification methods which are used for separation of lipophilic metabolites produced by microorganisms are employed, for instance extraction with a water-immiscible organic solvent and adsorption by activated carbon or a nonionic macroporous resin.

The organic solvent to be used for said extraction includes esters, such as ethyl acetate and n-butyl acetate, alcohols, such as i-butanol, halogenated hydrocarbons, such as methylene chloride, and ketones, such as methyl isobutyl ketone.

Specifically, the culture broth is filtered, the filtrate is made neutral or weakly acidic and extracted with an organic solvent such as ethyl acetate, and the extract is treated with an oxidizing agent such as ferric chloride or a reducing agent such as sodium hydrosulfite and then concentrated under reduced pressure. Addition of a nonpolar solvent such as hexane gives a crude product. The desired compound or compounds are isolated from the crude product suitably by adsorption chromatography using such a carrier as silica gel or alumina. Specifically, said compound or compounds can be isolated, for instance, by column or thin layer chromatography using silica gel with a mixed solvent, such as an ethyl acetate-n-hexane or chloroform-methanol system.

The six O-demethylated products which can be isolated by the above method can respectively be recovered in the crystalline form from ethyl acetate, an ethyl acetate-n-hexane mixture or a methylene chloride-n-hexane mixture, for instance.

The physico-chemical properties 21-O-demethylmacbecin I, C-33196 E-5 and C-33196 E-3 as obtained in Example 2 are shown in Table 1 and Table 2.

TABLE 1

| | 21-O—demethylmacbecin I |
|---|---|
| Melting point | >300° C. |
| Mass spectrum ($M^+$) | m/z 544 |
| Ultraviolet absorption spectrum $\lambda_{max}^{MeOH}$ ($E_{1\ cm}^{1\%}$) | 274 nm (440) |
| | 397 nm (45.3) |
| Infrared absorption spectrum $\nu_{max}^{KBr}$ | 1730, 1705, 1655 |
| | 1615, 1510, 1095 cm$^{-1}$ |
| $R_f$ values in thin layer chromatography (silica gel) | |
| (1) Chloroform-methanol (9:1) | 0.63 |
| (2) Ethyl acetate-n-hexane (4:1) | 0.31 |

TABLE 2

| | C-33196 E-5 | C-33196 E-3 |
|---|---|---|
| Melting point | 115–116° C. | >300° C. |
| $[\alpha]_D^{25}$ (CHCl$_3$) | +287.4° | +290.0° |

TABLE 2-continued

|  | C-33196 E-5 | C-33196 E-3 |
|---|---|---|
| Mass spectrum (M+) | m/z 544 | m/z 544 |
| Elemental analysis (%) |  |  |
| Molecular formula | $C_{29}H_{40}N_2O_8 \cdot CH_3COOC_2H_5$ | $C_{29}H_{40}N_2O_8$ |
| Calculated |  |  |
| C | 62.64 | 63.95 |
| H | 7.65 | 7.40 |
| N | 4.43 | 5.14 |
| Found |  |  |
| C | 62.74 | 63.87 |
| H | 7.46 | 7.39 |
| N | 4.34 | 5.33 |
| Ultraviolet absorption spectrum $\lambda_{max}^{MeOH}$ (E$_{1\,cm}^{1\%}$) | 274 nm (412) 397 nm (41.0) | 274 nm (455) 397 nm (47.5) |
| Infrared absorption spectrum $\nu_{max}^{KBr}$ | 1740, 1705, 1670, 1660, 1615, 1510, 1095 cm$^{-1}$ | 1740, 1700, 1655, 1610, 1510, 1095 cm$^{-1}$ |
| R$_f$ values in thin layer chromatography (silica gel) |  |  |
| (1) Chloroform-methanol (9:1) | 0.65 | 0.70 |
| (2) Ethyl acetate-n-hexane (4:1) | 0.23 | 0.36 |

The physico-chemical characteristics of 21-O-demethylmacbecin II, C-33196 E-5-R and C-33196 E-3-R as obtained in Example 3 are shown in Table 3 and Table 4.

TABLE 3

|  | 21-O—demethylmacbecin II |
|---|---|
| Mass spectrum (M+) | m/z 546 |
| Ultraviolet absorption spectrum $\lambda_{max}^{MeOH}$ (E$_{1\,cm}^{1\%}$) | 255 nm (278) 306 nm (82) |
| Infrared absorption spectrum $\nu_{max}^{KBr}$ | 1715, 1650, 1595, 1530, 1450, 1375, 1320, 1090, 1035 cm$^{-1}$ |
| R$_f$ values in thin layer chromatography (silica gel) |  |
| (1) Chloroform-methanol (9:1) | 0.29 |
| (2) Ethyl acetate-n-hexane (4:1) | 0.10 |

TABLE 4

|  | C-33196 E-5-R | C-33196 E-3-R |
|---|---|---|
| Melting point | 142–143° C. | 224–225° C. |
| [α]$_D^{25}$ (MeOH) | +59.6° | +51.6° |
| Mass spectrum (M+) | m/z 546 | m/z 546 |
| Elemental analysis (%) |  |  |
| Molecular formula | $C_{29}H_{42}N_2O_8 \cdot H_2O \cdot \frac{1}{2}CH_3COOC_2H_5$ | $C_{29}H_{42}N_2O_8$ |
| Calculated |  |  |
| C | 61.26 | 63.72 |
| H | 7.79 | 7.74 |
| N | 4.61 | 5.12 |
| Found |  |  |
| C | 61.70 | 63.45 |
| H | 7.86 | 7.65 |
| N | 4.65 | 5.09 |
| Ultraviolet absorption spectrum $\lambda_{max}^{MeOH}$ (E$_{1\,cm}^{1\%}$) | 255 nm (288) 306 nm (72) | 255 nm (273) 306 nm (80) |
| Infrared absorption spectrum $\nu_{max}^{KBr}$ | 1715, 1640, 1595, 1530, 1460, 1380, 1320, 1085, 1035 cm$^{-1}$ | 1720, 1650, 1630, 1605, 1540, 1460, 1390, 1335, 1320, 1200, 1100, 1040 cm$^{-1}$ |
| R$_f$ values in thin layer chromatography (silica gel) |  |  |
| (1) Chloroform-methanol (9:1) | 0.45 | 0.49 |
| (2) Ethyl acetate-n-hexane (4:1) | 0.11 | 0.19 |

For each of the compounds 21-O-demethylmacbecin I, E-5 and E-3, the M+ is found at m/z 544 in the mass spectrum. Thus the compounds are isomers having the same molecular formula $C_{29}H_{40}N_2O_8$, which is less than the molecular formula for the starting compound (II), $C_{30}H_{42}N_2O_8$, by one $CH_2$ group. In $^1$H-NMR spectra, signals for three OCH$_3$ groups are found for compound (II) whereas two OCH$_3$ groups only are detected for each of the compounds 21-O-demethylmacbecin I, E-5 and E-3. Therefore, the latter compounds are regarded as O-demethylated products. The three demethylated products, i.e. 21-O-demethylmacbecin I, E-5 and E-3, are different in chemical shift due to the demethylated OCH$_2$ group. Their structures were respectively identified by a fine spin decoupling experiment and it was concluded that 21-O-demethylmacbecin I is a product of demethylation at position 21, E-5 a product of demethylation at position 18 and E-3 a product of demethylation at position 17.

Thus obtained benzoquinone compound [namely 21-O-demethylmacbecin I, E-5 or E-3] and hydroquinone compound [namely 21-O-demethylmacbecin II, E-5-R or E-3-R] are interconvertible.

The conversion of the benzoquinone form to the hydroquinone form can be carried out by a conventional method for the reduction of benzoquinones. Thus, for example, the reducing agent may be sodium hydrosulfite, sodium hydrogen sulfite, sodium borohydride or the like and the solvent may be any of solvents inert to the above reaction, such as esters (e.g. ethyl acetate), alcohols (e.g. methanol, ethanol) and water and mixtures of these. Furthermore, a binary system consisting of water and a water-immiscible organic solvent may also be used advantageously. The reaction is performed generally at a temperature of about 0°–40° C., normally at room temperature, and is complete in about 30 seconds to 24 hours depending on the reaction temperature.

For the conversion of the hydroquinone form to the benzoquinone form, any method conventionally used for the oxidation of hydroquinones is usable. Thus, for instance, the oxidizing agent includes ferric chloride, ferric sulfate, silver oxide and the like, and the solvent may be any of the solvents which do not interfere with the reaction, for example, an ester (e.g. ethyl acetate), a ketone (e.g. acetone), water, or a mixture of these. A binary solvent system consisting of water and a water-immiscible organic solvent may also be used favorably.

The reaction temperature is not critical and the reaction is carried out generally at about 0°–40° C., preferably at room temperature. Depending on the reaction temperature, the reaction easily comes to completion generally in about 30 seconds to 24 hours.

Thus obtained macbecin derivatives, i.e. compounds (I), having antibacterial, antifungal and antiprotozoal activities and expectedly have antitumor activity. Furthermore, they may be used as starting materials for the synthesis of useful derivatives.

E-5, E-5-R, E-3 and E-3-R each inhibits *Staphylococcus aureus* and *Bacillus subtilis*, the MIC being 50–100 mcg/ml. Therefore, they are usable as antibacterial agents. As regards the acute toxicity, the $LD_{50}$ value for E-5-R, for instance, is 100–200 mg/kg (mouse, ip) indicating low toxicity of said compound. The compounds (I) are believed to have low toxicity.

The compounds (I) of the present invention may be used as disinfectants in the form of ethanol-containing (e.g. 5 v/v percent ethanol-containing) aqueous solutions containing compounds (I) in a concentration of 10–100 μg/ml. Such solutions may be used for disinfection of birdcages, doghouses, barns, experimental appliances and apparatus, and so forth.

The microorganism to be used in carrying out the production of E-3, E-3-R, E-4, E-4-R, E-5, E-5-R, E-6, E-6-R, E-7 and/or E-7-R (those compounds are collectively called "Antibiotics C-33196 E-3 to E-7-R".) may be any of the microorganisms belonging to the genus Actinosynnema and capable of producing said antibiotic(s). A typical example is Actinosynnema sp. No. C-33196 strain (hereinafter also referred to as "strain C-33196").

The taxonomic characteristics of strain C-33196 were investigated by procedures analogous to those of Shirling and Gottlieb [International Journal of Systematic Bacteriology, vol. 16, pp. 313–340 (1966)]. The results of observations at 28° C. for 21 days are as follows.

(1) Morphological characteristics

The vegetative mycelium, which is colorless to pale yellow or orange-yellow, extends well and develops into branches, both on agar and in liquid media. The hyphae mostly measure 0.5 to 1.2 microns in diameter and, at later stages of incubation, fragment into bacillary or elongated bacillary elements or branched short lengths of hyphae. The strain gives good growth on various taxonomic media, with the growth of the aerial mycelium on the vegetative mycelium. In many cases, the aerial mycelia appear as if they had grown on a large number of coremia (50 to 180 μm×400 to 1,500 μm). Many of the aerial hyphae are flexuous or straight but some appear to be loosely spiral but on rare occasions. Microscopic examination of aged cultures reveals that in few cases do the spores occur apparently in chains, there being few of what are called conidia or spores. When examined under a microscope, a cell suspension sample taken from the surface of such a culture revealed the presence of many elongated ellipsoidal (0.5 to 1.2 μm×4.8 to 6.8 μm) and ellipsiodal (0.8 to 1.2 μm×1.5 to 4 μm) cells which looked like fragmented cells or arthrospores, the surface of which were smooth as examined by electron microscopy. The aerial mycelium is generally sparse and, although fair growth is noted on many media over 3 to 7 days of incubation, it sometimes disappears as cultivation is carried out for more than 10 days.

When aged aerial mycelia are immersed in a liquid medium, motile cells liberate after 15–30 minutes. Electron microscopic examination of these motile cells reveals long peritrichous flagella around the cells. When cultivated in liquid media, the strain in later phases of incubation sometimes form polymorphic fragmented hyphae, some of which are motile.

(2) Cell constituents

The strain was shake-cultured in modified ISP No. 1 medium at 28° C. for 66–99 hours and, in the well grown stationary phase, the cells were collected and rinsed. By the method of B. Becker et al. [Applied Microbiology, vol. 12, p. 421 (1964)] and the method of M. P. Lechevalier [Journal of Laboratory and Clinical Medicine, vol. 71, p. 934 (1968)], the above cells were examined for diaminopimelic acid and sugar composition. The former was found to be the meso form and, as to the latter, a spot corresponding to galactose was observed. A cell wall sample was prepared by the method of B. Becker et al. [Applied Microbiology, vol. 13, p. 236 (1965)] and analyzed for diaminopimelic acid, sugars and amino acids. As regards diaminopimelic acid, the meso form was detected. Regarding sugars, a large amount of galactose was found, while arabinose was not detected. As to amino acids, glutamic acid and alanine were clearly detected, although lysine and glycine could be found only in traces. Thus, the strain belongs to type III in cell wall type classification.

(3) Cultural characteristics on taxonomic media

The strain gives comparatively good growth invariably on various media and the color of the vegetative mycelium is colorless to pale yellow in the early phases of incubation but is pale yellowish brown to yellowish brown in later stages. The organism does not produce soluble pigments in most taxonomic media. The aerial mycelia is powdery, generally grows to a moderate extent, and represents white to yellow or pale yellowish brown color. The aerial mycelium disappears on many media on prolonged culture (approximately two weeks or more), with the surface of vegetative mycelium beginning to become glossy. The cultural features of this particular strain on various taxonomic media are summarized below in Table 5.

Table 5 Cultural characteristics of strain C-33196 on taxonomic media (A) Sucrose nitrate agar:
  Growth (G): Moderate, thin, light ivory (2ca)*
  Aerial mycelium (AM: Scant, white
  Soluble pigment (SP): None
(B) Glycerol nitrate agar:
  G: Moderate, light ivory (2ca)*
  AM: Scant, white
  SP: None
(C) Glucose asparagine agar:
  G: Moderate, yellow (3ga)*, coremium-like bodies formed
  AM: Scant, light melon yellow (3ea)*
  SP: None
(D) Glycerol asparagine agar:
  G: Moderate, light ivory (2ca)*, coremium-like bodies formed
  AM: Scant, white to light ivory (2ca)*
  SP: None
(E) Nutrient agar:
  G: Abundant, bright yellow (21a)*
  AM: None
  SP: None
(F) Calcium malate agar:
  G: Scant, light ivory (2ca)*
  AM: Scant, white
  SP: None
(G) Yeast extract-malt extract agar:

G: Abundant, bright yellow (31a)*
AM: Scant, white
SP: None
(H) Oatmeal agar:
G: Moderate, light wheat (2ea)*, coremium-like bodies formed
AM: Scant, white
SP: None
(I) Inorganic salt starch agar
G: Moderate, light ivory (2ca)* to light melon yellow (3ea)*
AM: Scant, light wheat (2ea)*
SP: None
(J) Peptone yeast extract iron agar:
G: Moderate, bright yellow (31a)*
AM: None
SP: None
(K) Tyrosine agar
G: Moderate, bright yellow (31a)*
AM: Scant, white
SP: None

*The color codes according to Color Harmony Manual, 4th ed. (Container Corporation of America, 1958).

(4) Physiological characters

The physiological characteristics of the strain are shown below in Table 6. The temperature range for growth is 12° C. to 35° C. The temperature range in which good aerial growth occurs on agar (ISP No. 2) is 16° C. to 32° C.

TABLE 6

Physiological characteristics of strain C-33196

| Temperature range for growth: | 12° C. to 35° C. |
| Temperature range for aerial growth: | 16° C. to 32° C. |
| Liquefaction of gelatin: | Positive |
| Hydrolysis of starch: | Positive |
| Reduction of nitrates: | Positive |
| Peptonization of milk: | Positive |
| Coagulation of milk: | Negative |
| Decomposition of casein: | Positive |
| Production of melanoid pigments: | Negative |
| Decomposition of tyrosine: | Positive |
| Decomposition of xanthine: | Negative |
| Decomposition of hypoxanthine: | Negative |
| Tolerance to lysozyme: | Positive |
| Tolerance to sodium chloride: | 2% |

(5) Utilization of various carbon sources

The utilization of various carbon sources was investigated using a basal medium containing 0.05% asparagine, 0.05% dipotassium phosphate, 0.02% magnesium sulfate, 0.001% ferrous sulfate, 0.1% ammonium sulfate and 2% agar. The results obtained are shown below in Table 7.

TABLE 7

Utilization of carbon sources by strain C-33196

| Source of carbon | Growth | Source of carbon | Growth |
|---|---|---|---|
| D-Xylose | ++ | Trehalose | ++ |
| L-Arabinose | ± | Raffinose | ++ |
| D-Glucose | ++ | Melibiose | ++ |
| D-Galactose | ++ | i-Inositol | ± |
| D-Fructose | ++ | D-Sorbitol | ± |
| L-Rhamnose | ++ | D-Mannitol | ++ |
| D-Mannose | ++ | Glycerol | + |
| Sucrose | ++ | Soluble starch | ++ |
| Maltose | + | Control | ± |

TABLE 7-continued

Utilization of carbon sources by strain C-33196

| Source of carbon | Growth | Source of carbon | Growth |
|---|---|---|---|
| Lactose | ++ | | |

Note:
++: Luxuriant growth
+: Moderate growth
±: Poor growth (6) Other characteristics The cells were harvested by the procedure previously described in (2) and DNA was prepared by a procedure analogous to that of J. Marmur et al. [Journal of Molecular Biology, vol. 3, p. 208 (1961)]. The G-C (Guanine-Cytosine) content of the DNA was found to be about 72 mole %.

Gram staining of the vegetative mycelium of this strain was positive.

The above characteristics of strain C-33196 were compared with the descriptions of S. A. Waksman's "The Actinomycetes, Vol. 2" (The Williams and Wilkins Co., 1961); R. E. Buchanan and N. E. Gibbons (ed.), "Bergey's Manual of Determinative Bacteriology, 8th ed, 1974"; and other literature references.

The above observations (1) that the strain in later phases of vegetative propagation form polymorphic fragmented hyphae, in some of which motility is observed, (2) that peritrichous motile cells form from mature aerial hyphae, (3) that aerial hyphae form coremia or synnemata on some of the agar media and (4) that the strain belongs to cell wall type III, coupled with other characteristics, clearly indicate that the strain belongs to the genus Actinosynnema. Therefore, the inventors named this strain Actinosynnema sp. No. C-33196.

The genus Actinosynnema is a genus of the order Actinomycetales and the bacterial characteristics thereof are reported by Hasegawa et al. in International Journal of Systematic Bacteriology, vol. 28, pp. 304-310 (1978) and are also described in the same journal, vol. 30, p. 245 (1980).

The strain C-33196 was deposited on August 11, 1981 at the Institute for Fermentation, Osaka, Japan (IFO) under the accession number of IFO 14127, and deposited on Aug. 26, 1981 at the Fermentation Research Institute, the Agency of Industrial Science and Technology, Ministry of International Trade and Industry, Japan (FRI) under the accession number of FERM P-6138, the deposit being converted to a deposit under the Budapest Treaty, and has been stored at FRI under the accession number of FERM BP-166.

Generally, microorganisms of the genus Actinosynnema are labile in their properties and may undergo mutations spontaneously or under the influence of mutagens. Thus, for example, the many mutant strains which are obtainable by irradiation with X-rays, gamma rays, ultraviolet radiation, etc., by monospore isolation, by culture on media containing various chemicals, or by any other mutagenesis-inducing means as well as the mutants spontaneously obtained from the strain should not be considered to represent any other distinct species in comparison with the above-mentioned bacteriological properties, but any of such mutants and variants, if capable of producing said antiobiotics, may be invariably utilized for the purpose of this invention. By way of example, various mutagenesis-inducing treatments of a strain capable of producing said antibiotics can yield mutants which produce light yellow to light yellowish brown or brown soluble pigments, mutants which give colorless vegetative mycelia, mutants which give reddish brown to orange red vegetative mycelia, mutants which give yellowish green vegetative mycelia or soluble pigments, mutants which give abundant white aerial mycelia, and mutants whose mycelia are apt to fragment.

The medium to be used in the cultivation of a microorganism capable of producing said antibiotics may be either in the liquid or in the solid state provided that it contains nutrients utilizable by said microorganism, although a liquid medium is preferred for large scale operations. Suitably formulated into the medium are carbon and nitrogen sources assimilable or digestible by the microorganism capable of producing said antibiotics, inorganic substances and trace nutrients. Examples of the carbon source are glucose, lactose, sucrose, maltose, dextrin, starch, glycerol, mannitol, sorbitol, fats and oils (e.g. soybean oil, lard oil, chicken oil), and n-paraffin. Examples of the nitrogen source are meat extract, yeast extract, dried yeast, soybean meal, corn steep liquor, peptone, cottonseed flour, spent molasses, urea, and ammonium salts (e.g. ammonium sulfate, ammonium chloride, ammonium nitrate, ammonium acetate). The medium may further contain salts of sodium, potassium, calcium, magnesium, etc., salts of iron, manganese, zinc, cobalt, nickel and other metals, salts of phosphoric acid, boric acid, etc., and salts of organic acids such as acetic acid and propionic acid. Furthermore, the medium may contain amino acids (e.g. glutamic acid, aspartic acid, alanine, lysine, methionine, proline), peptides (e.g. dipeptides, tripeptides), vitamins (e.g. $B_1$, $B_2$, nicotinic acid, $B_{12}$, C), nucleic acids (e.g. purine, pyrimidine, derivatives thereof) and so forth. Naturally, there may be added an inorganic or organic acid, an alkali or a buffer or the like for the purpose of adjusting the pH of the medium and/or a fat or oil, a surfactant or the like in an adequate amount for the purpose of defoaming.

The cultivation may be conducted by any of the stationary, shake, submerged aerobic and other cultural methods. For big-volume production runs, the so-called submerged aerobic culture is of course preferred. While the conditions of culture naturally depend upon the conditions and composition of the medium, type of the strain, cultural method and other factors, it is normally preferable to carry out incubation at a temperature of about 20° C. to 32° C. with an initial pH of about neutral. Particularly desirable is a temperature from about 25° C. to 28° C. in an intermediate stage of cultivation, with an initial pH of about 6.5 to 7.5. While the incubation time also depends on the same factors as mentioned above, it is advisable to continue the incubation until the titer of the desired anitibiotic becomes maximal. In the case of shake culture or submerged aerobic culture in a liquid medium, the time required normally ranges from about 48 to 96 hours.

Said antibiotics produced in the culture broth can be recovered by a procedure adequately selected from among the procedures normally utilized in the isolation and purification of metabolites produced by microorganisms, since said antibiotics are neutral and liposoluble. For instance, the means utilizing the difference in solubility from impurities, adsorption chromatography using a variety of adsorbents such as activated carbon, nonionic macroporous resins, silica gel and alumina and other means are used alone or in combination.

While said antibiotics occur primarily in the culture broth filtrate, they can be extracted also from the cells as necessary. For the extraction from the microbial cells, a water-miscible organic solvent, such as a lower alcohol (e.g. methanol, ethanol) or a ketone (e.g. acetone, methyl ethyl ketone) or a mixture thereof with water may be used. The extraction may also be effected with a water-immiscible organic solvent, such as ethyl acetate or a like ester. Furthermore, the antibiotics can be extracted by adding a water-miscible organic solvent, such as methanol or acetone, to the whole culture broth.

For the recovery of said antibiotics from the culture broth filtrate, there may be employed water-immiscible organic solvents such as fatty acid esters (e.g. ethyl acetate, butyl acetate), alcohols (e.g. butanol), halogenated hydrocarbons (e.g. chloroform) and ketones (e.g. methyl isobutyl ketone). Said antibiotics can be obtained in the crude state by washing the extract with water, concentrating the same and adding n-hexane or the like. In case one of said antibiotics is the principal constituent, i.e. contained in a larger amount, it may sometimes be isolated in the crystalline form by the mere procedure of extraction with an organic solvent, followed by concentration.

Said antibiotics can also be recovered from the culture broth by adsorption on a nonionic macroporous resin such as Diaion HP-10 (Mitsubishi Chemical Industries, Japan) followed by elution with an aqueous alcohol or ketone or the like.

When the crude product obtained in the above manner from the culture broth through the steps of extraction, concentration and so on is a mixture of said antibiotics, a variety of adsorption chromatography techniques may be used for the separation of the components. The adsorbent may be a conventional carrier such as silica gel, alumina or an adsorbent resin or reversed phase carrier such as μBondapak $C_{18}$ (Waters Associates Inc. USA).

When the adsorbent is silica gel, development is generally conducted with a combination of a polar organic solvent and a nonpolar organic solvent, for example a mixed solvent composed of ethyl acetate and n-hexane or of methanol and chloroform, for separating the components from one another. For instance, the components may be separated by first conducting development with a nonpolar solvent and then effecting elution while increasing the proportion of a polar solvent stepwise. In case the crude powdery product is a multicomponent mixture and/or contains impurities in relatively large amounts, the respective components may be separated from one another by repeating chromatography with varied combinations of organic solvents.

Said antibiotics include the benzoquinone form and the hydroquinone form, which are convertible to each other. Therefore, for the purpose of purification, it is advantageous to reduce the number of components to half by converting the hydroquinone form to the benzoquinone form or the benzoquinone form to the hydroquinone form by oxidation or reduction, respectively.

The oxidation can be carried out by a method generally used for the oxidation of hydroquinones. Thus, the oxidizing agent is, for example, ferric chloride, ferric sulfate, potassium ferricyanide or silver oxide, and the solvent may be any of the solvents inert to the reaction, for example an ester such as ethyl acetate, a ketone such as acetone, water, or a mixture of these. Furthermore, a binary system consisting of water and a water-immiscible organic solvent also may favorably be used. The reaction temperature is not critical but the reaction is generally carried out at about 0°–40° C., preferably at room temperature, and easily comes to completion generally in about 30 seconds to 24 hours depending on the reaction temperature.

The reduction is carried out in a manner conventional for the reduction of benzoquinones. Thus, the reducing agent includes sodium hydrosulfite, sodium hydrogen sulfite and sodium borohydride, and the solvent includes any solvents inert to the reaction, such as esters (e.g. ethyl acetate), alcohols (e.g. methanol, ethanol), water, and mixed solvents composed of these. Furthermore, a binary system consisting of water and a water-immiscible organic solvent also may favorably be used. The reaction is carried out generally at a temperature of about 0°–40° C., preferably at room temperature, and the reaction easily comes to completion in about 30 seconds to 24 hours depending on the reaction temperature.

In performing silica gel chromatography, the antibiotics are purified generally in the benzoquinone form. In some instances, however, the hydroquinone form is convenient for the purpose of purification. Therefore, the components should be separated by adequately selecting either the oxidation or the reduction method with due regard to the impurities in the mixture and contents thereof.

Thus obtained components can be crystallized from an appropriate solvent such as ethyl acetate, methanol, methylene chloride or methanol-water.

The physico-chemical characteristics of Antibiotic C-33196E-4 and Antibiotic C-33196E-4-R, which contains one molecule of ethyl acetate as the solvent of crystallization, as obtained in Example 8 and Example 6 to be mentioned hereinbelow are shown in Table 8.

TABLE 8

| | Antibiotic C-33196 E-4 | Antibiotic C-33196 E-4-R |
|---|---|---|
| Melting point | 209–210° C. | 224–225° C. |
| Appearance | Yellow crystals | Colorless crystals |
| $[\alpha]_D^{25}$ | +53.8° (c = 0.5, CHCl$_3$) | +32° (c = 0.5, MeOH) |
| Elemental analysis (%) | | |
| C | 62.94 | 61.34 |
| H | 7.63 | 8.16 |
| N | 5.24 | 4.66 |
| Mass spectrum (M$^+$) | m/z 532 | m/z 534 |
| Expected molecular formula | C$_{28}$H$_{40}$N$_2$O$_8$ | C$_{28}$H$_{42}$N$_2$O$_8$·CH$_3$COOC$_2$H$_5$ |
| Ultraviolet absorption spectrum $\lambda_{max}^{MeOH}$ (E$_{1\ cm}^{1\%}$) | 276 nm (272) 390 nm (33.5) | 307 nm (75) |
| Infrared absorption spectrum $\nu_{max}^{KBr}$ | 1735, 1700, 1670 1650, 1625, 1605 1500, 1380, 1305 1290, 1210, 1050 cm$^{-1}$ | 1720, 1670, 1630, 1600, 1535, 1465, 1380, 1325, 1045 cm$^{-1}$ |
| Solubility | | |
| Sparingly soluble in | Petroleum ether, hexane, water. | Petroleum ether, hexane, diethyl ether, chloroform, ethyl acetate. |
| Soluble in | Chloroform, methylene chloride, toluene, diethyl ether. | Methanol. |
| Readily soluble in | Acetone, ethyl acetate, methanol, dimethyl sulfoxide. | Dimethyl sulfoxide. |

TABLE 8-continued

| | Antibiotic C-33196 E-4 | Antibiotic C-33196 E-4-R |
|---|---|---|
| Color reactions | | |
| Positive | Potassium permanganate test (decoloration) | Barton reaction, potassium permanganate test (decoloration). |
| Negative | Ninhydrin, Ehrlich, Barton. | Ninhydrin, Ehrlich. |
| Thin layer chromatography (TLC) (Rf) | | |
| Chloroform-methanol (9:1) | 0.52 | 0.27 |
| Ethyl acetate-n-hexane (4:1) | 0.27 | 0.12 |
| Acidity, neutrality or basicity | Neutral | Neutral |

The physico-chemical properties of Antibiotics C-33196 E-6 and E-6-R as obtained in Example 11 and those of Antibiotics C-33196 E-7 and E-7-R as obtained in Example 10 are shown in Table 9 and Table 10, respectively.

TABLE 9

| | C-33196 E-6 | C-33196 E-6-R |
|---|---|---|
| Melting point | >300° C. | 176–177° C. |
| Color | yellow | colorless |
| $[\alpha]_D^{24}$ | +258.8° C. (c = 0.5, CHCl$_3$) | +37.8° (c = 0.5, MeOH) |
| Elemental analysis (%) | | |
| C | 63.49 | 61.35 |
| H | 7.28 | 7.52 |
| N | 5.27 | 5.07 |
| Mass spectrum | m/z 530 (M$^+$) | m/z 532 (M$^+$) |
| Ultraviolet absorption spectrum $\lambda_{max}^{MeOH}$ (E$_{1\ cm}^{1\%}$) | 273 nm (454) 397 nm (50.3) | 255 nm (337) 307 nm (91) |
| Infrared absorption spectrum (principal peaks) $\nu_{max}^{KBr}$ | 1720, 1705, 1670, 1650, 1610, 1505, 1380, 1325, 1265, 1210, 1090, 1040 cm$^{-1}$ | 1720, 1650, 1600, 1535, 1460, 1380, 1320, 1090, 1040, 1010 cm$^{-1}$ |
| Solubility | | |
| Hardly soluble | petroleum ether, n-hexane, water. | petroleum ether, n-hexane, diethyl ether, water. |
| Soluble | diethyl ether, ethyl acetate. | ethyl acetate. |
| Readily soluble | chloroform, methanol, acetone, dimethylsulfoxide | dimethyl sulfoxide, methanol. |
| Color reaction | | |
| Positive | Decoloration of potassium permanganese reagent. | Barton reaction, decoloration of potassium permanganese reagent. |
| Negative | Ninhydrin, Ehrlich, Barton, Greig Leaback reactions | Ninhydrin, Ehrlich, Greig Leaback reactions |
| Rf values in thin layer chromatography | | |
| chloroform-methanol (9:1) | 0.41 | 0.22 |
| ethyl acetate-n-hexane (4:1) | 0.14 | 0.06 |
| Acidic neutral or | neutral | neutral |

TABLE 9-continued

|  | C-33196 E-6 | C-33196 E-6-R |
|---|---|---|
| basic |  |  |

TABLE 10

|  | C-33196 E-7 | C-33196 E-7-R |
|---|---|---|
| Melting point | 158–159° C. | 205–206° C. |
| Color | yellow | colorless |
| $[\alpha]_D^{24}$ | +37.4° | +18.6° |
|  | (c = 0.5, CHCl$_3$) | (c = 0.5, MeOH) |
| Elemental analysis |  |  |
| C | 62.45 | 61.36 |
| H | 7.16 | 7.36 |
| N | 5.01 | 4.97 |
| Mass spectrum | m/z 530 (M$^+$) | m/z 532 (M$^+$) |
| Ultraviolet absorption spectrum | 274 nm (502) 396 nm (59.8) | 250 nm (305) 315 nm (68) |
| Infrared absorption spectrum, (principal peaks) $\nu_{max}^{KBr}$ | 1725, 1670, 1650, 1605, 1500, 1380, 1325, 1260, 1205, 1150, 1095, 1035 cm$^{-1}$ | 1710, 1640, 1600, 1485, 1455, 1380, 1310, 1250, 1090, 1040 cm$^{-1}$ |
| Solubility |  |  |
| Hardly soluble | petroleum ether, n-hexane, water. | petroleum ether, n-hexane, diethyl ether, water. |
| Soluble | diethyl ether, ethyl acetate. | ethyl acetate. |
| Readily soluble | chloroform, methanol, acetone, dimethylsulfoxide. | dimethyl sulfoxide, methanol. |
| Color reaction |  |  |
| Positive | Decoloration of potassium permanganese reagent. | Barton reaction, decoloration of potassium permanganese reagent. |
| Negative | Ninhydrin, Ehrlich, Barton, Greig Leaback reactions | Ninhydrin, Ehrlich, Barton, Greig Leaback reactions |
| Rf values in thin layer chromatography |  |  |
| chloroform-methanol (9:1) | 0.65 | 0.18 |
| ethyl acetate-n-hexane (4:1) | 0.65 | 0.06 |
| Acidic, neutral or basic | neutral | neutral |

The nuclear magnetic resonance (NMR) spectrum is shown in Table 11.

TABLE 11

| $^1$H—NMR spectrum (deuterio acetone) (90 MHz) | |
|---|---|
|  | E - 6 | E - 7 |
| δ (ppm) | 0.87 (3H,d) | 0.75 (3H,d) |
|  | 0.97 (3H,d) | 1.17 (3H,d) |
|  | 1.03 (3H,d) | 1.25 (3H,d) |
|  | 1.63 (3H,bs) | 1.70 (3H,bs) |
|  | 1.94 (3H,bs) | 1.98 (3H,bs) |
|  | 3.29 (3H,s) | 3.31 (3H,s) |
|  | 4.81 (1H,m) | 4.63 (1H,m) |
|  | 5.30 (1H,bs) | 4.98 (1H,bs) |
|  | 5.66 (1H,t) | 5.62 (1H,bd) |
|  | 5.82 (2H,bs) | 5.75 (2H,bs) |
|  | 5.85 (1H,d) | 5.83 (1H,t) |
|  | 6.31 (1H,t) | 6.38 (1H,t) |
|  | 6.63 (1H,dd) | 6.68 (1H,t) |
|  | 7.20 (1H,bd) | 7.20 (1H,bd) |
|  | 7.23 (1H,d) | 7.27 (1H,d) |

TABLE 11-continued

| $^1$H—NMR spectrum (deuterio acetone) (90 MHz) | |
|---|---|
| E - 6 | E - 7 |
| 8.94 (1H,s) | 8.73 (1H,s) |

Note:
s: singlet,
d: doublet,
t: triplet,
m: multiplet,
b: broad.

Based on the above physico-chemical properties and NMR spectral data, it is presumed that the antibiotics of the invention, namely C-33196E-6, E-6-R, E-7 and E-7-R, have the following general formula

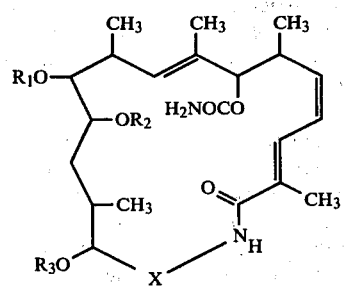

wherein $R_1$, $R_2$, $R_3$ and X are as defined above. It is also presumed that, in E-6 and E-7, X is

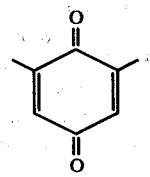

and, in E-6-R and E-7-R, X is

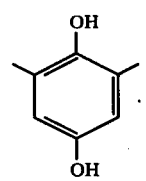

In view of the above, the antibiotics of the invention, i.e. C-33196E-6, E-6-R, E-7 and E-7-R, are presumably novel compounds as judged from their physicochemical properties, NMR spectra and structural formulas.

As regards the mixture containing at least two of the members of Antibiotics C-33196 E-3 to E-7-R, the proportion between or among the components constituting said mixture is not critical, but, for instance, the amount of one component each of the mixture is not less than about 5%.

Antibiotics C-33196 E-3 to E-7-R have antibacterial, antifungal and antiprotozoal activities. Since they exhibit cytocidal effects against tumor cells, they are expected to have antitumor activity. Furthermore, they may be used as the starting materials in the synthesis of useful derivatives.

Antibiotics C-33196 E-3 to E-7-R, whose MICs against *Staphylococcus aureus* and *Bacillus subtilis* are 50 to 100 mcg/ml, are almost comparable in antibacterial activity against said species to Macbecin I and II. In testing by the broth dilution method, E-6 and E-7 inhibits the growth of *Tetrahymena pyriformis* W at 10 μg/ml and 40 μg/ml, respectively. Therefore, Antibiotics C-33196 E-3 to E-7-R can be used as antibacterial and antiprotozoal agents.

As regards the acute toxicity, the $LD_{50}$ of E-5-R, for instance, is 100 to 200 mg/kg (mouse, intraperitoneal), indicating its lower toxicity as compared with Macbecin I and II. The Antibiotic C-33196E-7-R has low toxicity as evidenced by the acute toxicity data, i.e. an intraperitoneal $LD_{50}$ in mice of not less than 400 mg/kg. Therefore, Antibiotics C-33196 E-3 to E-7-R are believed to be low in acute toxicity.

Antibiotics C-33196 E-3 to E-7-R can be used as disinfectants for the disinfection of birdcages, experimental appliances and apparatus, barns, cattle sheds and so forth, for example in the form of 10 to 100 μg/ml solutions in ethanol-containing water.

The following examples illustrate the invention in more detail. Unless otherwise stated, "percent (%)" means "weight/volume percent".

EXAMPLE 1

A medium (pH 7.2) containing 1% dextrin, 1% glucose, 1% glycerol, 0.5% peptone, 0.5% yeast extract, 0.5% meat extract, 0.3% sodium chloride and 0.5% precipitated calcium carbonate was inoculated with *Streptomyces platensis* IFO 12901, and shaking culture was performed at 28° C. for 17 hours. Macbecin I (1.9 g) was added to 20 liters of the culture broth obtained, and the reaction was carried out at 28° C. with shaking for 24 hours. The culture broth after the reaction had a decreased Macbecin I content and contained O-demethylated products, as evidenced by thin layer chromatography (TLC).

EXAMPLE 2

The filtrate obtained by filtration of 20 liters of the reaction culture broth as obtained in Example 1 with Hyflo Super Cel (Johns Manville, USA) added to said broth was adjusted to pH 6.0 and extracted with two 10-liter portions of ethyl acetate. The extract was washed with water and concentrated to 1 liter. Thereto was added 500 ml of 2% aqueous ferric chloride solution and the mixture was stirred for an hour. Then, the ethyl acetate layer was washed twice with water and concentrated. Addition of n-hexane gave 1.45 g of a crude powder.

The crude powder was subjected to column chromatography using 65 g of silica gel (E. Merck A. G., West Germany) and eluted first with n-hexane (200 ml) and then with hexane-ethyl acetate mixtures [1:1 (300 ml), 1:2 (300 ml), 1:4 (300 ml) and 1:9 (300 ml) in sequence], whereby the remaining starting material (Macbecin I), E-3, 21--O-demethylmacbecin I and E-5 were eluted in that order. Each fraction was checked by thin layer chromatography, and the fractions containing each single compound were concentrated. There were thus obtained 43 mg of 21-O-demethylmacbecin I, 248 mg of E-5 and 111 mg of E-3.

EXAMPLE 3

Macbecin II (1 g) was added to 10 liters of the culture broth as obtained in Example 1, and the reaction was carried out at 28° C. with shaking for 24 hours. It was confirmed by TLC that Macbecin II had been converted to O-demethylated compounds in the reaction culture broth.

Following addition of Hyflo Super Cel, 10 liters of the reaction culture broth was filtered, and the filtrate was adjusted to pH 6.0 and extracted with two 3.5-liter portions of ethyl acetate. The extract was washed with water and concentrated to 1 liter. Following addition of 500 ml of 2% aqueous ferric chloride solution, the mixture was stirred for an hour. Thereafter, the ethyl acetate layer was washed with water and concentrated. Upon addition of n-hexane, there was obtained 610 mg of a crude powder.

This powder was subjected to column chromatography using 30 g of silica gel (E. Merck A. G., West Germany) and eluted with n-hexane, n-hexane-ethyl acetate (1:1), n-hexane-ethyl acetate (1:2), h-hexane-ethyl acetate (1:4) and n-hexane-ethyl acetate (1:9) in that order. The n-hexane-ethyl acetate (1:2) elution fractions were concentrated to dryness, the residue was dissolved in ethyl acetate, reduced with 2% aqueous sodium hydrosulfite, washed with water and concentrated to give 62 mg of E-3-R.

The n-hexane-ethyl acetate (1:4) elution fractions were concentrated to dryness, and the residue was further purified by preparative TLC using silica gel (E. Merck A. G., West Germany) (n-hexane-ethyl acetate=1:4), then dissolved in ethyl acetate and reduced with 2% aqueous sodium hydrosulfite. The ethyl acetate layer was washed with water and concentrated to give 23 mg of 21-O-demethylmacbecin II.

The n-hexane-ethyl acetate (1:9) elution fractions from the silica gel column were concentrated to dryness and the residue, following purification by the similar silica gel preparative TLC (n-hexane-ethyl acetate=1:4), was dissolved in ethyl acetate and reduced with 2% aqueous $Na_2S_2O_4$. The ethyl acetate layer was washed with water and concentrated to give 116 mg of E-5-R.

EXAMPLE 4

*Nocardia mediterranei* IFO 13415 was shake-cultured in a medium containing 1% glucose, 1% Tryptone (Difco, USA) and 0.6% yeast extract at 30° C. for 2 days. The culture broth was used to inoculate a fermentation medium having the same composition as above at the inoculum size of 5%. After incubation at 30° C. for 24 hours, the fermentation broth obtained was centrifuged and the cells thus collected were washed with sterile water and suspended in sterile water in an amount of one fifth of the fermentation broth to give a suspension of washed cells. To 4.5 ml of this cell suspension were added 0.2 ml of 1 M phosphate buffer (pH 7.0) and 0.2 ml of a 20 mg/ml Macbecin I solution in methanol. The reaction was carried out in a test tube at 30° C. with shaking for 20 hours. The liquid reaction mixture was extracted with an equal amount of ethyl acetate, the extract was washed with water, two volumes of 2% aqueous ferric chloride was added, and the mixture was stirred. Thereafter, 5 μl of the ethyl acetate layer was spotted on a silica gel plate (E. Merck A. G., $60F_{254}$) and developed with water-saturated ethyl acetate. Assaying using a Shimadzu dual-wavelength TLC scanner CS-910 (Shimadzu Seisakusho Ltd., Japan) revealed 80% conversion of the Macbecin I fed to O-demethylated compounds.

EXAMPLE 5

Macbecin I (500 mg) was added to 1.3 liters of the fermentation broth as obtained by the procedure of Example 4, the reaction was carried out at 30° C. with shaking for 20 hours. The liquid reaction mixture was filtered, and the filtrate was adjusted to pH 6.5 and extracted with two 650-ml portions of ethyl acetate. The extract was washed with water, 1.1 liters of 2% aqueous ferric chloride, and the mixture was stirred for an hour. Thereafter, the ethyl acetate layer was washed twice with water and concentrated. Upon addition of n-hexane, there was obtained 400 mg of a crude powder.

The crude powder (400 mg) was subjected to column chromatography using 65 g of silica gel (Merck) and developed in sequence with n-hexane and 2:1, 1:1, 1:2 and 1:4 n-hexane-ethyl acetate mixtures. The fractions containing the main reaction product were combined and concentrated to dryness and further subjected to silica gel (40 g) column chromatography, followed by development with n-hexane and chloroform-methanol (100:1→100:2→100:3) mixtures in that order. The single-spot fractions were combined and concentrated almost to dryness, and the residue was dissolved in ethyl acetate. Upon cooling, there was obtained 84 mg of E-3 as yellow crystals. A second crop (51 mg) of E-3 was recovered from the mother liquor.

EXAMPLE 6

A seed culture medium (pH 7.0) in a 200-ml Erlenmeyer flask, which contained 2% glucose, 3% soluble starch, 1% raw soybean flour, 1% corn steep liquor, 0.5% peptone, 0.3% NaCl and 0.5% $CaCO_3$, was inoculated with Actinosynnema sp. No. C-33196 (IFO 14127, FERM BP-166) grown on yeast extract-malt extract-agar, and incubation was carried out on a rotary shaker at 28° C. for 48 hours. A 10-ml portion of the thus-obtained culture broth was transferred to a 2-liter Sakaguchi flask containing 500 ml of the same seed culture medium. Incubation was performed on a reciprocal shaker at 28° C. for 48 hours. One liter of the thus-obtained culture broth was used to inoculate 100 liters of the same seed culture medium in a 200-liter stainless steel tank. Incubation was conducted at 28° C. and aeration rate of 100 liters per minute with stirring at 200 revolutions per minute for 48 hours, whereby a seed culture broth was obtained. A 60-liter portion of the seed culture broth was transferred to a 2,000-liter stainless steel tank containing 1,200 liters of a fermentation medium containing 5% glycerol, 2% corn steep liquor, 2% dried yeast, 0.5% $MgCl_2$, 2% $KH_2PO_4$ and 0.1% $CaCO_3$, and incubation was performed at 28° C. and aeration rate of 1,200 liters per minute with stirring at 150 revolutions per minute under an inside pressure of 1 kg/cm$^2$ for 114 hours. The fermentation broth (1,100 liters) was filtered with 61.8 kg of Hyflo Super Cel. The filtrate and washings were combined (1,200 liters), adjusted to pH 6.5 and extracted with 600 liters of ethyl acetate. The extract was washed with water and concentrated under reduced pressure to about 40 liters, when 20 liters of 2% aqueous ferric chloride was added. Then, the mixture was stirred for an hour. After the oxidation process, the ethyl acetate layer was washed with two 20-liter portions of water and then concentrated under reduced pressure. The oily residue (about 200 ml) was washed with two one-liter portions of n-hexane. To the residue (about 100 ml) was added 500 ml of ethyl acetate and the mixture was allowed to stand in a cool place, whereby crystals precipitated. The crystals were filtered off, and the mother liquor was concentrated and the residue was subjected to column chromatography using 450 g of cilica gel (E. Merck A. G.). The column was washed with n-hexane (500 ml) and then developed in sequence with h-hexane-ethyl acetate (4:1→2:1→1:1→1:2→1:4→1:8) mixtures. E-3 was found in the n-hexane-ethyl acetate (1:2) elution fractions, antibiotic C-33196E-4 in the n-hexane-ethyl acetate (1:4) fractions, and E-5 in the n-hexane-ethyl acetate (1:8) fractions.

Each of the thus-obtained products was not composed of a single component as yet and accordingly was purified once more by silica gel chromatography.

The mixture whose major component was E-3 was adsorbed on a 100 g silica gel column and developed with hexane, chloroform and chloroform-methanol (100:1→25:1) in that order. Concentration of the combined fractions each showing a single spot in TLC gave 66 mg of E-3. The mother liquor was subjected to reduction with 2% aqueous sodium hydrosulfite. The reduction product was subjected to column chromatography using silica gel (100 g). Development with hexane, chloroform and chloroform-methanol (50:1→50:4) in that order and concentration of the fractions showing a single spot in TLC gave 170 mg of E-3-R in the crystalline form.

The mixture whose major component was antibiotic C-33196E-4 was adsorbed on a silica gel (150g) column and developed in sequence with hexane, chloroform and chloroform-methanol (50:1→10:1). The desired product-containing fractions were combined and concentrated, the residue was dissolved in ethyl acetate and treated with 2% aqueous sodium hydrosulfite. The reduction product was again subjected to silica gel (130 g) column chromatography. Development with hexane, chloroform and chloroform-methanol (25:1→5:1) in that order followed by combining and concentration of the single-spot fractions gave crystals (430 mg) of antibiotic C-33196E-4-R.

The fraction in which E-5 was the major component was adsorbed on a 200 g silica gel column and developed in sequence with hexane, chloroform and chloroform-methanol (25:1→10:1). The E-5 containing fractions were combined and concentrated, the residue was dissolved in ethyl acetate and treated with 2% sodium hydrosulfite. The reduction product was subjected again to silica gel (130 g) column chromatography and developed with hexane, chloroform and chloroform-methanol (50:1→10:1) in that order. Concentration of the combined single-spot fractions gave crystals (1.325 g) of E-5-R.

EXAMPLE 7

Methanol (1 liter) was added to a one-liter portion of the fermentation broth as obtained in the same manner as in Example 6, and the mixture was filtered. The methanol was removed from the filtrate by distillation, the residue was adjusted to pH 6–7 and extracted with two 500-ml portions of ethyl acetate, and the extract was washed with water and concentrated. TLC of the concentrate confirmed the presence of Antiobiotic C-33196E-4, Antibiotic C-33196E-4-R, E-5, E-5-R, E-3 and E-3-R.

EXAMPLE 8

In 100 ml of ethyl acetate was dissolved 100 mg of Antibiotic C-33196E-4-R as obtained in Example 6. Thereto was added 50 ml of 2% aqueous ferric chloride and the mixture was stirred for an hour. Thereafter, the ethyl acetate was separated, washed with water and concentrated to give 88 mg of Antibiotic C-33196E-4.

EXAMPLE 9

E-5-R and E-3-R as obtained in Example 6 were treated in the same manner as in Example 8 to give E-5 and E-3, respectively, each in the crystalline form.

The physico-chemical characteristics of E-5 and E-3 as obtained in Example 6 and Example 9, and those of E-5-R and E-3-R are identical with those obtained in Examples 2 and 3.

EXAMPLE 10

A seed culture medium (pH 7.0) in a 200-ml Erlenmeyer flask, which contained 2% glucose, 3% soluble starch, 1% raw soybean flour, 1% corn steep liquor, 0.5% peptone, 0.3% NaCl and 0.5% $CaCO_3$, was inoculated with Actinosynnema sp. No. C-33196 (IFO 14127, FERM BP-166) grown on yeast extract-malt extract agar, and incubation was carried out on a rotary shaker at 28° C. for 48 hours. A 10-ml portion of the thus-obtained culture broth was transferred to a 2liter Sakaguchi flask containing 500 ml of the same seed culture medium. Incubation was performed on a reciprocal shaker at 28° C. for 48 hours. One liter of the thus-obtained culture broth was used to inoculate 100 liters of the same seed culture medium in a 200-liter stainless steel tank. Incubation was conducted at 28° C. and aeration rate of 100 liters per minute with stirring at 200 revolutions per minute for 48 hours, whereby a seed culture broth was obtained. A 60-liter portion of the seed culture broth was transferred to a 2,000-liter stainless steel tank containing 1,200 liters of a fermentation medium containing 5% glycerol, 2% corn steep liquor, 2% dried yeast, 0.5% $MgCl_2$, 2% $KH_2PO_4$ and 0.1% $CaCO_3$, and incubation was performed at 28° C. and aeration rate of 1,200 liters per minute with stirring at 150 revolutions per minute under an inside pressure of 1 $kg/cm^2$ for 114 hours. The fermentation borth (1,100 liters) was filtered with 61.8 kg of Hyflo Super Cel. The filtrate and washings were combined (1,200 liters), adjusted to pH 6.5 and extracted with 650 liters of ethyl acetate.

Thin layer chromatography [eluant: chloroformmethanol (9:1)]of the extract revealed the presence of E-7 ($R_f$: 0.65) and E-7-R ($R_f$: 0.18).

For easier isolation and purification of the desired products, E-7-R in the extract was once oxidized to E-7, which was then purified and further reduced to E-7-R. Thus, the extract was washed with 300 liters of water and then concentrated under reduced pressure (to 28 liters). Thereto was added 14 liters of 2% aqueous ferric chloride solution and the mixture was stirred. An hour later, the ethyl acetate layer was washed with two 14-liter portions of water and concentrated. The oily concentrate was washed with four 500-ml portions of n-hexane, and the remaining viscous residue was dissolved in 500 ml of ethyl acetate. The solution was mixed with 250 g of silica gel (Kieselgel 60, E. Merck A. G., Federal Republic of Germany). The resulting mixture was concentrated to dryness and placed on a silica gel (500 g) column. The whole column was washed with n-hexane and eluted in sequence with n-hexane-ethyl acetate mixtures (4:1→2:1→1:1→1:2→1:4→1:8). The 2:1→1:1 n-hexane-ethyl acetate elution fractions contained C-33196E-7. These fractions were combined and concentrated to about 50 ml and further diluted with 200 ml of ethyl acetate. Thereafter, 120 ml of 2% aqueous sodium hydrosulfite solution was added and the mixture was stirred. After removing the aqueous layer, the reduction treatment was repeated once more in the same manner. The organic layer was washed with water, dried and concentrated under reduced pressure to 20 ml. Then, 10 g of silica gel was added and the mixture was concentrated to dryness. The residue was placed on a silica gel (50 g) column. Following developing with n-hexane, the whole column was eluted in sequence with chloroform and chloroform-methanol mixtures (100:1→50:1→4:1). The 4:1 chloroform-methanol elution fractions which contained C-33196E-7-R were concentrated under reduced pressure and the residue was dissolved in ethyl acetate. Upon cooling, the solution yielded 423 mg of C-33196E-7-R as colorless crystals.

Dissolution of 200 mg of C-33196E-7-R in 100 ml of ethyl acetate, oxidation with 100 ml of 2% aqueous ferric chloride solution, washing with water, concentration and addition of n-hexane gave 180 mg of C-33196E-7 as a yellow powder.

EXAMPLE 11

Each of 2-ml aliquots of the seed culture obtained by Erlenmeyer flask cultivation in Example 10 was transplanted to a 200-ml Erlenmeyer flask containing 40 ml of main culture medium containing 5% glycerol, 2% dried yeast, 2% corn steep liquor and 3% monoammonium phosphate (pH 7.0). Incubation was carried out on a rotary shaker at 28° C. for 90 hours. Five liters of the culture broth was filtered with Hyflo Super Cel and the filtrate was adjusted to pH 7 and extracted with two 2.5-liter portions of ethyl acetate.

Thin layer chromatography [eluent: chloroform-methanol (9:1)] revealed the presence of E-6 ($R_f$: 0.41) and E-6-R ($R_f$: 0.22).

For convenience of isolation of the desired products, E-6-R contained in the extract was oxidized to E-6, which was isolated and purified together with the E-6 originally produced by the microorganism. Thus, after washing with water, the ethyl acetate layer was concentrated to 1 liter, 500 ml of 2% aqueous ferric chloride solution, the mixture was stirred for an hour, and then the ethyl acetate layer was washed with water and concentrated. To the concentrate (about 30 ml) was added 10 g of silica gel, the mixture was again concentrated to dryness, and the residue was placed on a silica gel (50 g) column.

The whole silica gel column was developed in sequence with n-hexane, chloroform and chloroform-methanol mixtures (100:1→30:1). The E-6-containing fractions (confirmed by thin layer chromatography) were combined and concentrated to give 160 mg of C-33196E-6 as yellow crystals.

To the mother liquor was added 5 g of silica gel, the mixture was concentrated to dryness, the residue was placed on a silica gel (25 g) column. The whole column was developed in the same manner as above. The E-6-containing elution fractions were concentrated, dissolved in 100 ml of ethyl acetate and reduced with two 50-ml portions of 2% sodium hydrosulfite. The ethyl acetate layer was washed with water, dried and concentrated to give 45 mg of C-33196E-6-R as colorless crystals.

What we claim is:

1. A compound represented by the formula:

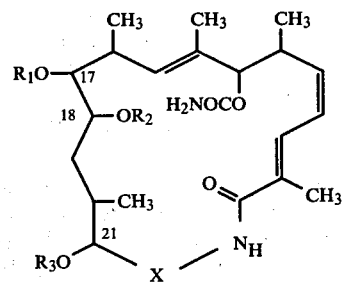

wherein one of the groups of $R_1$, $R_2$ and $R_3$ is hydrogen, and the remaining ones are methyl, and X is a group of

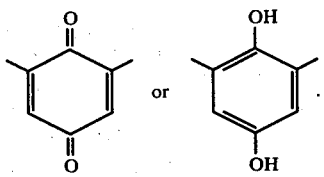

2. A compound as claimed in claim 1, wherein $R_1$ is methyl, $R_2$ is methyl, $R_3$ is hydrogen and X is

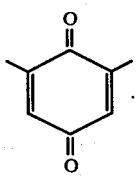

3. A compound as claimed in claim 1, wherein $R_1$ is methyl, $R_2$ is methyl, $R_3$ is hydrogen and X is

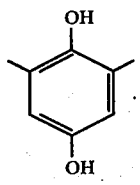

4. A compound as claimed in claim 1, wherein $R_1$ is methyl, $R_2$ is hydrogen, $R_3$ is methyl and X is

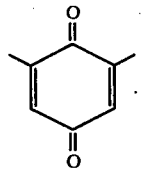

5. A compound as claimed in claim 1, wherein $R_1$ is methyl, $R_2$ is hydrogen, $R_3$ is methyl and X is

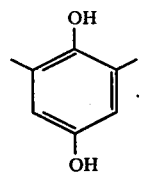

6. A compound as claimed in claim 1, wherein $R_1$ is hydrogen, $R_2$ is methyl, $R_3$ is methyl and X is

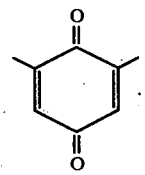

7. A compound as claimed in claim 1, wherein $R_1$ is hydrogen, $R_2$ is methyl, $R_3$ is methyl and X is

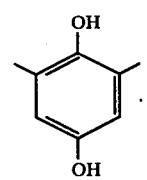

* * * * *